United States Patent [19]
Chen

[11] Patent Number: 6,068,986
[45] Date of Patent: May 30, 2000

[54] ANTIBODIES SPECIFIC FOR D-MYO-INOSITOL 1,4,5-TRISPHOSPHATE AND THE ENZYME-LINKED IMMUNOSORBENT ASSAY OF D-MYO-INOSITOL 1,4,5-TRISPHOSPHATE

[75] Inventor: Ching-Shih Chen, Wakefield, R.I.

[73] Assignee: The Board of Governors for Higher Education, Providence, R.I.

[21] Appl. No.: 08/956,893

[22] Filed: Oct. 23, 1997

Related U.S. Application Data

[62] Division of application No. 08/584,095, Jan. 11, 1996, Pat. No. 5,798,447, which is a continuation of application No. 08/331,924, Oct. 31, 1994, abandoned, which is a continuation-in-part of application No. 08/181,188, Jan. 13, 1994, Pat. No. 5,393,912.

[51] Int. Cl.$^7$ .................................................. G01N 33/53
[52] U.S. Cl. ..................... 435/7.92; 435/7.1; 436/543; 436/547; 436/528; 436/532
[58] Field of Search .................... 435/7.1, 7.92; 436/543, 547, 528, 532

[56] References Cited

U.S. PATENT DOCUMENTS 5,252,707  10/1993  Ozaki et al. .
5,393,912  2/1995  Chen et al. .

OTHER PUBLICATIONS

Gon et al., *Bioorg. Med. Chem*, vol. 2, No. 1, pp. 7–13.
Harlow & Lane, (1988) Antibodies, A Laboratory Manual, Cold Spring Harbor Laboratory, pp. 53–88, 127–137 and 309–315.

*Primary Examiner*—Toni R. Scheiner
*Attorney, Agent, or Firm*—Samuels, Gauthier & Stevens

[57] ABSTRACT

Antibodies against Ins(1,4,5)$P_3$ were raised by immunizing rabbits with two types of $IP_3$-BSA conjugates which were synthesized by covalently coupling Ins(1,4,5)$P_3$ to the carrier protein via alkyl linkages. The anti-Ins(1,4,5)$P_3$ antibodies were detected by an ELISA where Ins(1,4,5)$P_3$ was covalently attached to a microplate well surface. Both antiserum preparations showed specific binding with Ins(1,4,5)$P_3$. The specificity of these antibodies was enhanced by affinity purification for the antiserum through Ins(1,4,5)$P_3$-agarose chromatography. The affinity-purified antibodies have $IC_{50}$ values of 12 nM and 730 nM for Ins(1,4,5)$P_3$ and Ins(1,3,4,5)$P_4$, respectively. These antibodies showed many properties similar to those of biologically relevant receptors for Ins(1,4,5)$P_3$.

4 Claims, 3 Drawing Sheets

ANTIBODIES SPECIFIC FOR D-MYO-INOSITOL 1,4,5-TRISPHOSPHATE AND THE ENZYME-LINKED IMMUNOSORBENT ASSAY OF D-MYO-INOSITOL 1,4,5-TRISPHOSPHATE

This is a divisional of copending application(s) Ser. No. 08/584,095 filed Jan. 11, 1996 now U.S. Pat. No. 5,798,447, which is a continuation of Ser. No. 08/331,924, filed Oct. 31, 1994 now abandoned, which is a continuation-in-part Ser. No. 08/181,188, filed Jan. 13, 1994, now U.S. Pat. No. 5,393,912.

BACKGROUND AND BRIEF SUMMARY OF THE INVENTION

The intricate role of Ins(1,4,5)$P_3$ in modulating intracellular $Ca^{2+}$ homeostasis has been the focus of many recent investigations, Berridge, M. J. *Nature,* 1993, 361, 315, and references cited therein. It is well documented that the initial agonist-induced $Ca^{2+}$ release is derived from the $Ca^{2+}$-mobilizing action of Ins(1,4,5)$P_3$ on intracellular organelles whose exact nature is still in dispute, Meldolesi, J.; Villa, A.; Volpe, P.; Pozzan, T. *Advances in Second Messenger and Phosphoprotein Research*; Putney, J. W., Jr., Ed.; Raven Press: New York, 1992; Vol. 26, pp 187–208. While many researchers assert that IP$_3$-specific receptors distribute mainly on the membrane of the endoplasmic reticulum or nucleus, others suggest the locality on a more specialized endomembrane fraction, i.e., calciosomes, Volpe, P.; Kraus, K. H.; Sadamitsu, H.; Zorzato, F.; Pozzan, T.; Meldolesi, J.; Low, P. B. *Proc. Natl. Acad. Sci. USA,* 1988, 85, 1091–1095. These Ins(1,4,5)P$_3$-specific receptors are thought to function as a ligand-gated $Ca^{2+}$ channel, Gill, D. L.; Ghosh, T. K.; Takemura, H.; Hughes, A. R.; Horstman, D. A.; and Thastrup, O. (1989) *FASEB J.* 3, 1899–1905. Thus, an important issue to be addressed is the mechanism of interaction between the Ins(1,4,5)P$_3$-sensitive $Ca^{2+}$ pool and the plasma membrane.

In researching inositol phosphate-mediated $Ca^{2+}$ homeostasis, our effort has focused on the synthesis of endogenous inositol polyphosphates and the generation of anti-Ins(1,4,5)P$_3$ antibodies in view of their potential use as biological probes. Although antibodies to PIP and PIP$_2$ have been prepared through immunizing animals with inositol-phospholipids, Matuoka, K.; Fukami, K.; Nakanishi, O.; Kawai, S.; and Takenawa, T. (1988) *Science* 239, 640–643, or with those liposomes containing these compounds, Roerdink, F.; Berson, B. J.; Richard, R. L.; Swartz, G. M., Jr.; Alving, C. R. (1980) *FedProc.* 40, 996; Freidman, R. L.; Iglewski, B. H.; Roerdink, F.; and Alving, C. R. (1982) *Biophys. J.* 37, 23–24; Fukami, K.; Matsuoka, K.; Nakanishi, O.; Yamakawa, A.; Kawai, S.; and Takenawa, T. (1988) *Proc. Natl. Acad. Sci. USA* 85, 9057–9061; and Bate, C. A. W.; Taverne, J. Bootsma, H. J.; Mason, R. C. St. H.; Skalko, N.; Gregoriadis, G.; and Playfair, H. L. (1992) *Immunology* 76, 35–41, a similar strategy could not be employed for inducing anti-Ins(1,4,5)P$_3$ antibodies because of the vast difference in their water solubilities. Hence, the invention broadly embodies the preparation of highly specific anti-Ins(1,4,5)P$_3$ antibodies using two types of Ins(1,4,5)P$_3$-BSA conjugates shown below as antigens. The analogues shown in the conjugates below are disclosed in a copending application Ser. No. 08/181,188 filed Jan. 13, 1994 entitled D-Myo-Inositol 1,4,5-Trisphosphate Analogues, which application is hereby incorporated by reference in its entirety into this disclosure.

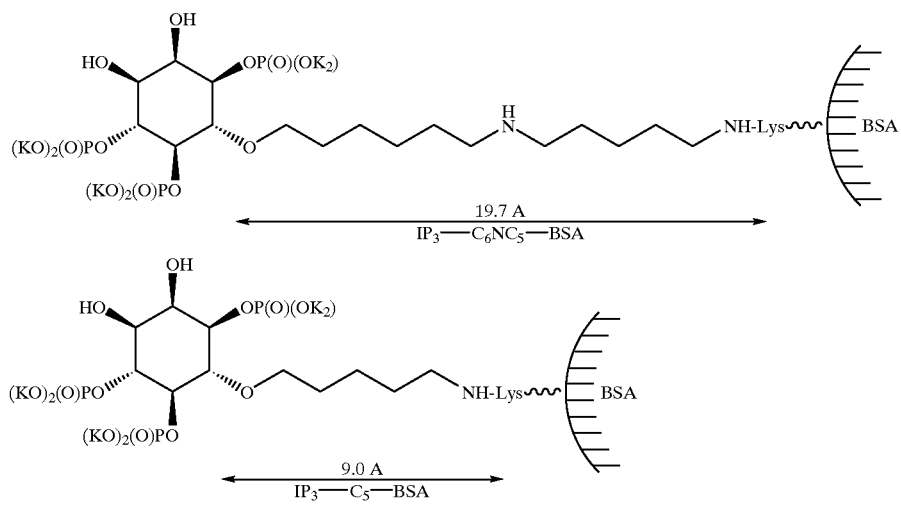

Bian, J.; Short, A. D.; Waldron, R. T.; and Rybank. S. L., *Advances in Second Messenger and Phosphoprotein Research,* 1992, Vol. 26, (Putney, J. W. ed), Raven Press, New York; pp. 265–308. In the second phase of the signaling process, i.e., $Ca^{2+}$ entry from the extracellular medium, Ins(1,4,5)P$_3$ has also been implicated. The capacitative entry theory suggests that depletion of the intracellular $Ca^{2+}$ store by Ins(1,4,5)P$_3$ generates a secondary signal of unknown nature that activates $Ca^{2+}$ entry, Putney, J. W., Jr. *Cell Calcium,* 1986, 7, 1–12; Takemura, H., and Putney, J. W., Jr. *Biochem. J.,* 1989, 258, 409–421; and Putney, J. W., Jr.;

The invention also embodies an affinity matrix for purifying Ins(1,4,5)P$_3$-specific antibodies and a unique ELISA system.

DESCRIPTION OF THE PREFERRED EMBODIMENT(S)

Figure 1A:
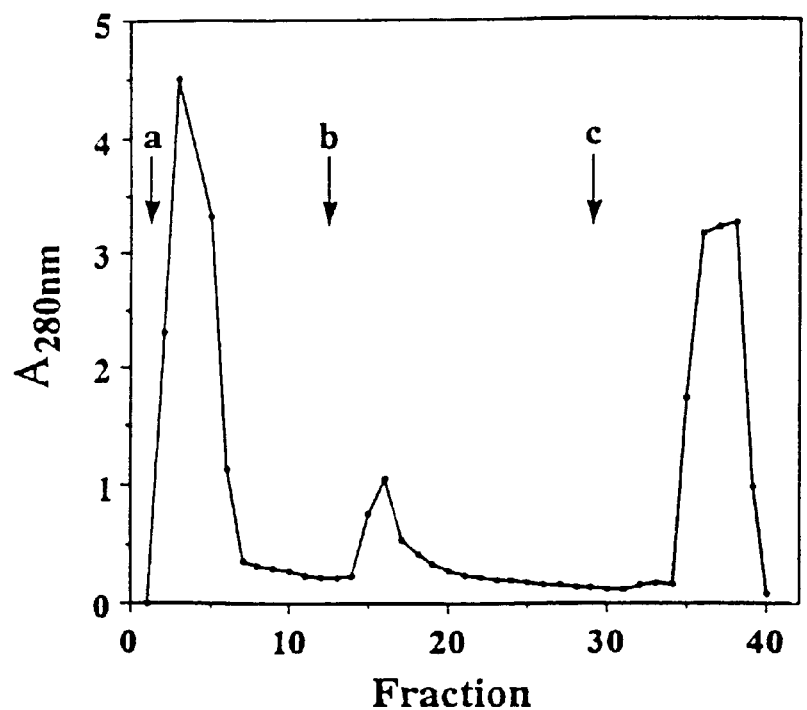
FIG. 1 is a graph of the affinity purification of Ins (1,4,5, P$_3$-specific antibodies)

The references cited in the following sections are hereby incorporated by reference in their entireties into this disclosure.

Materials

6-O-(ω-Aminohexyl)-D-myo-inositol 1,4,5-triphosphate 1 and 6-O-5',6'-dihydroxyhexyl)-2:3-O-cyclohexylidene-D-myo-inositol 1,4,5-triphosphate 2 were used for the preparation of $IP_3$-$C_6NC_5$-BSA and $IP_3$-$C_5$-BSA respectively. Both compounds were extensively characterized by $^1H$ and $^{31}P$ NMR and FAB mass spectrometry. Their synthesis is described hereinafter.

Ins(1,4,5)$P_3$, Ins(1,3,4)$P_3$, and Ins(1,3,4,5)$P_4$ were synthesized from optically active 1,2:5,6-di-O-cyclohexylidene-inositol (optical purity >98% e.e.) according to previously described procedures, Liu, Y.-C.; and Chen, C.-S. (1989) *Tetrahedron Lett.* 30, 1617–1620; Gou, D.-M.; and Chen, C.-S. (1992) *Tetrahedron Lett.* 33, 721–724; and Gou, D.-M; Liu, Y.-C; and Chen, C.-S. (1992) *Carbohydr. Res.* 234, 51–64. Ins(4,5)$P_2$, Ins(1,5,6)$P_3$, Ins(1,2,5,6)$P_4$ were synthesized by following the same procedures with the following modifications. The chemical purity of these chiral inositol phosphates was greater than 98% according to $^1H$ and $^{31}P$ NMR spectroscopy. The amount of isomeric impurities was not detectable as indicated by these NMR spectra. Phytic acid, $PIP_2$, and Ins(1)$P_1$ were purchased from Sigma. Other chemicals and biochemicals were supplied from Sigma or Aldrich unless otherwise mentioned.

Preparation of Ins (1,4,5)$P_3$-agarose

Ins(1,4,5)$P_3$-agarose was prepared by reacting 1 with 1,1'-carbonyldiimidazole-activated 6% crosslinked beaded agarose (Reacti-Ge®; Pierce) according to the standard protocol recommended by Pierce Chemical Co. Instruction 20259 (1989) Reacti-Gel® (6X). In brief, activated Reacti-Gel® (6 ml) was thoroughly washed with distilled water, and was added to 10 mM borate buffer, pH 9.5, (15 ml) containing the $IP_3$ ligand (28 mg). The suspension was incubated at room temperature with gentle shaking for 25 hours. The reaction was terminated by adding 10 ml of 1 M Tris/HCl, pH 8.0, to the reaction mixture. The gel was recovered by filtration, thoroughly washed, and stored in 10 mM Tris/HCl, pH 7.5, containing 0.1% $NaN_3$ at 4° C.

Preparation of $IP_3$-BSA Conjugates and Immunization

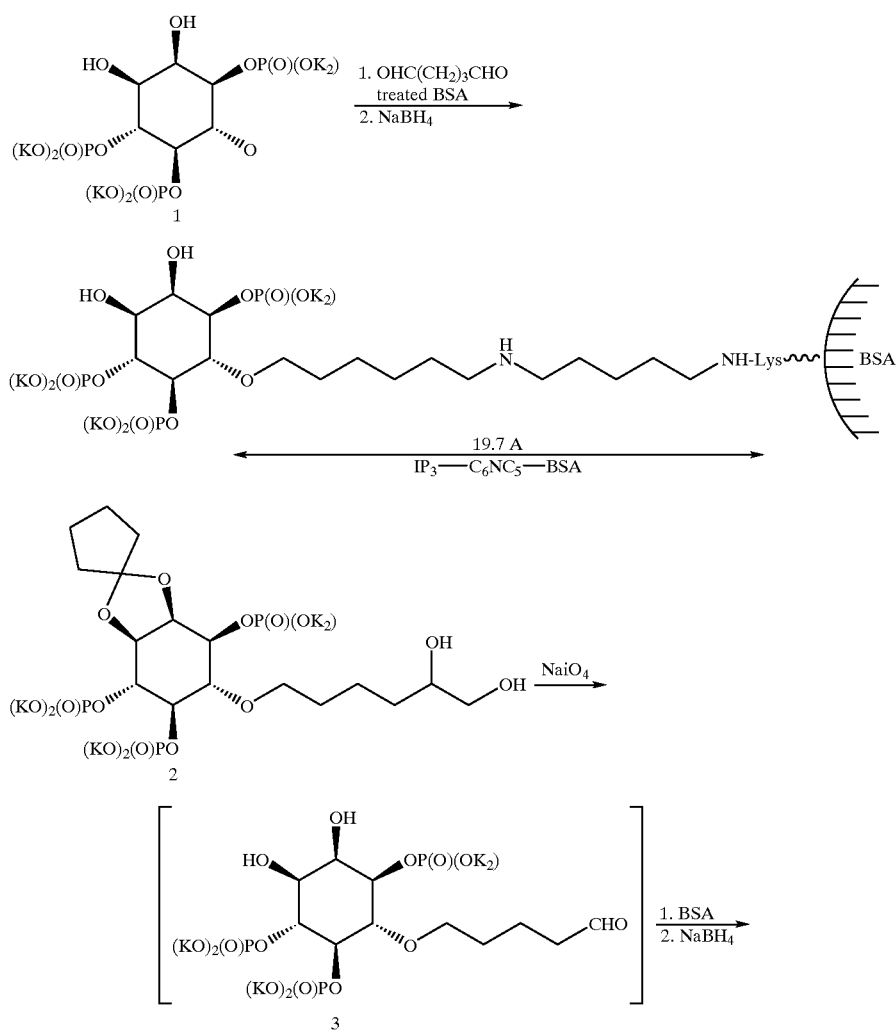

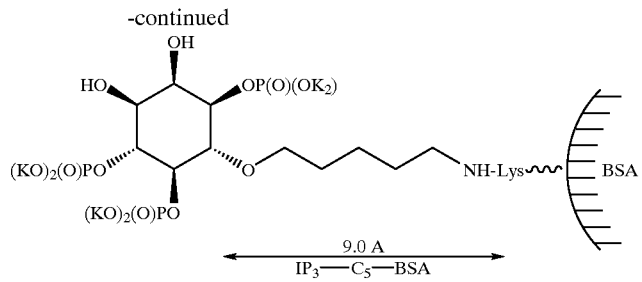

IP$_3$-C$_6$NC$_5$-BSA. 10% Glutaraldehyde (4 ml) was added dropwise to a solution of BSA (20 mg) in 10 mM NaHCO$_3$/Na$_2$CO$_3$ buffer, pH 9.5. The mixture was stirred at 5° C. for 40 minutes, and dialyzed against the same buffer overnight with at least three changes. 1 (20 mg) was then added, and the mixture was incubated at 15° C. After 3 hours, NaBH$_4$ (100 mg) was added, and the incubation continued at 15° C. for additional 3 hours. The solution was dialyzed against 10 mM NaHCO$_3$/CO$_2$ buffer, pH 7.0, overnight, and lyophilized to afford IP$_3$-C$_6$NC$_5$-BSA.

IP$_3$-C$_5$-BSA. NaIO$_4$ (12 mg, 0.06 mmol), dissolved in water (1 ml), was added in several portions to a solution of 2 (50 mg, 0.06 mmol) in distilled water (1 ml), pH 7.5, at 0° C. The mixture was stirred at 20° C. for 2.5 hours, and 1 N HCl (100 µl) was added. After stirring for an additional 2 hours, the solution was extracted with ethyl ether to remove cyclohexanone, adjusted to pH 8 with NaHCO$_3$, and lyophilized to afford 6-O-(4'-formylbutyl)-D-myo-inositol 1,4,5-triphosphate 3. The aldehyde intermediate, without purification, was incubated with BSA (20 mg) in 4 ml of 10 mM NaHCO$_3$/Na$_2$CO$_3$ buffer, pH 9.5, at 5° C. for 2 hours. NaBH$_4$ (20 mg) was then added, and the incubation continued at room temperature for an additional 2 hours. The reaction mixture was dialyzed against 10 mM NaHCO$_3$/CO$_2$ buffer, pH 7.4, overnight, and lyophilized to give IP$_3$-C$_5$-BSA.

Immunization

New Zealand White female rabbits were immunized with 1 mg of the IP$_3$-BSA conjugate in 0.5 ml of saline emulsified with an equal volume of Freund's complete adjuvant by five to six subcutaneous injections at the back and both flanks. Booster injections were given with the same amounts of the IP$_3$-BSA prepared with incomplete Freund's adjuvant at monthly intervals. After the second boost, the animals were bled from the ear vein 2 weeks after each booster injection. The antisera thus prepared were stored at −20° C. until used.

ELISA

The presence of anti-Ins(1,4,5)P$_3$ antibodies in rabbit serum was detected by an ELISA. Ins(1,4,5)P$_3$ (hapten) was covalently attached to microtiter plates through a C-6 linker by adding 6-O-(ω-Aminohexyl)-D-myo-inositol 1,4,5-triphosphate (1) (1.25 µg in 0.1 ml of phosphate buffered saline (PBS) per well) to maleic anhydride-activated polystyrene plates (Pierce). This anhydride-activated plate allows direct coupling of amine-bearing molecules to the well surface, (Pierce Chemical Co. Instruction 15110X (1992) Reacti-Bind™ Maleic Anhydride Activated Polystyrene Plates), and obviates the need for a carrier protein to immobilize haptens. The plate was incubated at room temperature overnight, and each well was blocked by adding 0.12 ml of SuperBlock blocking solution in PBS (Pierce). After 10 minutes at room temperature, the plate was washed twice with 0.05% Tween-20 in 10 mM Tris/HCl containing 0.85% NaCl, pH 7.2 (TBS), followed by TBS buffer twice. Rabbit antiserum (antibodies) diluted in TBS buffer containing 0.1% gelatin was added (95 µl per well). The plate was incubated at 37° C. for 2 hours, and washed as stated above. Specific antibody binding was assessed by adding goat anti-rabbit IgG-HRP conjugate (1/200 dilution in TBS containing 0.1% gelatin; 90 µl per well), and the plate was incubated for another 2 hours at 37° C. After the plate was washed again, the peroxidase substrate solution (90 µl per well) containing 2 mM 2,2'-azinobis(3-ethyl-benzthiazoline-6-sulfonic acid), 2.5 mM hydrogen peroxide, and 50 mM citrate buffer, with a final pH of 5.0, was added. The reaction was incubated at room temperature for 15–20 minutes, and terminated by adding 20 µl of 5% SDS to each well. The absorbance at 415 nm was measured by a microtiter plate reader. Rabbit serum taken before immunization was used as a control in all the assays, from which the absorbance values obtained served as a blank for the correction of experimental data.

Purification of Ins(1,4,5)P$_3$-specific Antibodies

Protein A column chromatography (step 1)—The antiserum (5.2 ml) was applied to an Econo-Pac protein A cartridge (5 ml, Bio-Rad) equilibrated with 100 mM Tris/HCl, pH 8.0. The column was washed with, in sequence, 20 ml of the equilibrating buffer, and 25 ml of 10 mM Tris/HCl, pH 8.0. The bound IgG was eluted with 25 ml of 100 mM glycine buffer, pH 3.0, at a flow rate of 0.5 ml/min. Fractions of 1.7 ml were collected in tubes containing 100 µl of 1 M Tris/HCl, pH 8.0. Fractions 36–38, exhibiting anti-Ins(1,4,5)P$_3$ antibody activity were collected, concentrated by ultrafiltration, and dialyzed against 10 mM Tris/HCl, pH 7.5.

Ins(1,4,5)IP$_3$-agarose chromatography (step 2)—The dialyzed solution from step 1 was applied to a Ins(1,4,5)IP$_3$-agarose column (5.8 ml bed volume) equilibrated with 10 mM Tris/HCl, pH 7.5. The column was washed with the equilibration buffer followed by 500 mM NaCl in the same buffer. The absorbed proteins were eluted with, in sequence, 50 ml of 100 mM glycine buffer, pH 3.5, 10 ml of 10 mM Tris/HCl, pH 8.8, and 50 ml of 100 mM NaHCO$_3$/Na$_2$CO$_3$ buffer, pH 10.5 Fractions of 1.7 ml were collected. For the eluate with the glycine buffer and with the NaHCO$_3$/Na$_2$/CO$_3$ buffer, fractions were collected in tubes containing 100 µl of 1 M Tris/HCl, pH 8.0, and 700 µl of 1 M Tris/HCl, pH 7.6, respectively. Fractions 66–69, exhibiting anti-Ins(1,4,5)IP$_3$ antibody activity, were pooled, concentrated, and dialyzed against 10 mM Tris/HCl, pH 7.5.

Results

Preparation of Antigens

The design of the Ins(1,4,5)P$_3$ analogues, 1 and 2, as haptens was based on: (a) the strategic importance of the C-2,3, cis-dihydroxyl groups, especially the axial 2-OH, in recognizing the microenvironments surrounding the phosphate functions, and (b) the potential steric effect of the linker on epitope recognition. The amine-bearing derivative 1 crosslinked to BSA using glutaraldehyde as a coupling agent, followed by in situ NaBH$_4$ reduction, to afford IP$_3$-C$_6$NC$_5$-BSA. On the other hand, the vicinal diol 2 was subjected to sodium periodate oxidation to yield the aldehyde intermediate, which, without purification, was coupled to the amino functions of the carrier protein. In situ $NaBH_4$ reduction of the shiff base yielded $IP_3$-$C_5$-BSA. The phosphorous contents of $IP_3$-$C_6$-$NC_5$-BSA and $IP_3$-$C_5$-BSA, determined by elemental analysis, were 2.9% and 0.67%, respectively. Accordingly, the molar ratios of the bound Ins(1,4,5)$P_3$ to BSA were estimated to be 22 and 5, respectively.

Anti-Ins(1,4,5)$P_3$ Antisera

Three New Zealand rabbits were immunized with $IP_3$-$C_6NC_5$-BSA, and a fourth one was injected with $IP_3$-$C_5$-BSA. The antibodies in the rabbit sera were detected by an ELISA where Ins(1,4,5)$P_3$ was covalently attached to the well surface through a C-6 linkage by reacting 1 with maleic anhydride-activated polystyrene plates. This antibody capture immunoassay provided a straightforward and consistent analysis of the antisera, and obviated tedious procedures associated with radioactive binding assays. Moreover, this assay avoided interference caused by nonspecific antibodies. For instance, an analysis using conventional EIA plates coated with Ins(1,4,5)$P_3$-$C_6NC_5$-casein was interfered by concomitant binding of the $C_6NC_5$-linker-directed antibodies to the exposed spacer on the carrier protein. As a consequence, this conventional assay did not respond to competitive inhibition by free Ins(1,4,5)$P_3$ in a quantitative manner.

After 2–3 times of booster injections, one of the rabbits immunized with $IP_3$-$C_6NC_5$-BSA and the rabbit receiving $IP_3$-$C_5$-BSA were found to produce antibodies against Ins(1,4,5)$P_3$, both with similar titers of about 1:4,000. This antibody formation seemed to be independent of spacer length and $IP_3$ content. The antibody titers increased only moderately in both rabbits after subsequent booster injections. It appeared that the remaining two rabbits which received $IP_3$-$C_6NC_5$-BSA immunization generated antibodies predominantly directed against the $C_6NC_5$-linker.

The avidity and specificity of these antisera were examined by competitive ELISA experiments between immobilized Ins(1,4,5)$P_3$ and various inositol phosphates. As indicated from the concentrations at half-maximal absorbance ($B/B_o$=0.5) or $IC_{50}$ (Table 1), for the $IP_3$-$C_6NC_5$-BSA induced antiserum, the affinity toward various inositol phosphates was in the order of: Ins(1,4,5)$P_3$>Ins(1,3,4,5)$P_4$>>Ins(1,3,4)$P_3$>Ins(3,4,5,6)$P_4$>Ins(1,5,6)$P_3$, $PIP_2$, Ins(1,2,5,6)$P_4$>Ins(4,5)$P_2$>$IP_6$>Ins(1)$P_1$.

TABLE 1

| Competitor | [Competitor] (M) at half maximal absorbance ($B/B_o$ = 0.5) | |
|---|---|---|
| | $IP_3$-$C_6$-$NC_5$-BSA induced antibodies | $IP_3$-$C_5$-BSA induced antibodies |
| (1,4,5)$IP_3$ | 8.9 × 10$^{-8}$ | 3.1 × 10$^{-8}$ |
| (1,3,4,5)$IP_4$ | 2.0 × 10$^{-7}$ | 7.1 × 10$^{-8}$ |
| (1,3,4)$IP_3$ | 1.7 × 10$^{-6}$ | 1.0 × 10$^{-5}$ |
| (3,4,5,6)$IP_4$ | 4.5 × 10$^{-6}$ | 6.3 × 10$^{-6}$ |
| $PIP_2$ | 1.6 × 10$^{-5}$ | 3.2 × 10$^{-5}$ |
| (1,2,5,6)$IP_4$ | 2.1 × 10$^{-5}$ | 7.1 × 10$^{-5}$ |
| (4,5)$IP_2$ | 3.8 × 10$^{-5}$ | 2.5 × 10$^{-5}$ |
| $IP_6$ | 1.5 × 10$^{-4}$ | 8.0 × 10$^{-4}$ |
| (1)$IP_1$ | 4.2 × 10$^{-4}$ | N.D. |

Table Legend

Table 1. Avidity of antisera toward various inositol phosphates and $PIP_2$. The avidity is expressed as the concentrations at half-maximal absorbance ($B/B_o$ = 0.5) in the competitive ELISA experiments.

The recognition of inositol phosphates by the $IP_3$-$C_5$-BSA induced antiserum qualitatively paralleled that mentioned above (Table 1). But, the $IP_3$-$C_5$-BSA induced antibodies exhibited stronger binding toward both Ins(1,4,5)$P_3$ and Ins(1,3,4,5)$P_4$ and a 10-fold decrease in affinity with Ins(1,3,4)$P_3$.

Although these antisera were highly specific for Ins(1,4,5)$P_3$, they also cross-reacted with Ins(1,3,4,5)$P_4$. The ratios of $IC_{50}^{[Ins(1,3,4,5)P_4]}$ to $IC_{50}^{[Ins(1,4,5)P_3]}$ were 2.2 and 2.3 for the antisera against $IP_3$-$C_6NC_5$-BSA and $IP_3$-$C_5$-BSA respectively.

Purification of Ins (1,4,5)$P_3$-specific Antibodies

The level of discrimination between Ins(1,4,5)$P_3$ and Ins(1,3,4,5)$P_4$ by these antisera appeared to be lower than that reported for Ins(1,4,5)$P_3$ receptors, Guillemette, B.; Balla, T., Baukal, J.; and Catt, K. J. (1988) *J. Biol. Chem.* 263, 4541–4548; Supattapone, S.; Worley, P. F.; Baraban, J. M.; and Snyder, S. H. (1988) *J. Biol. Chem.* 263, 1530–1534; and Ferris, D. C.; Huganir, R. L.; Supattapone, S.; and Snyder, S. H. (1989) *Nature* 342, 87–89. The lack of specificity could be attributed to the heterogeneity in the antigen binding sites. The $IP_3$-$C_5$-BSA induced antiserum was subjected to chromatographic purification on immobilized protein A and Ins(1,4,5)$P_3$-agarose. The utility of the $IP_3$ affinity column is especially noteworthy. The Ins(1,4,5)$P_3$-specific antibodies had strong binding with the affinity matrix, and could only be eluted under alkaline conditions.

Referring to FIG. 1(A), the $IP_3$-$C_5$-BSA induced antiserum (5.2 ml) was applied to an Econo-Pac protein A cartridge (5 ml, Bio-Rad) equilibrated with 100 mM Tris buffer, pH 8.0. The column was washed, in sequence, with (a) 20 ml of the equilibrating buffer, (b) 25 ml of 10 mM Tris buffer, pH 8.0, and (c) 25 ml of 100 mM glycine buffer, pH 3.0, at a flow rate of 0.5 ml/min. Fractions of 1.7 ml were collected Fractions 36–38, exhibiting anti-Ins(1,4,5)$IP_3$ antibody activity, were pooled, concentrated and dialyzed against 10 mM Tris buffer, pH 7.5.

Figure 1B:
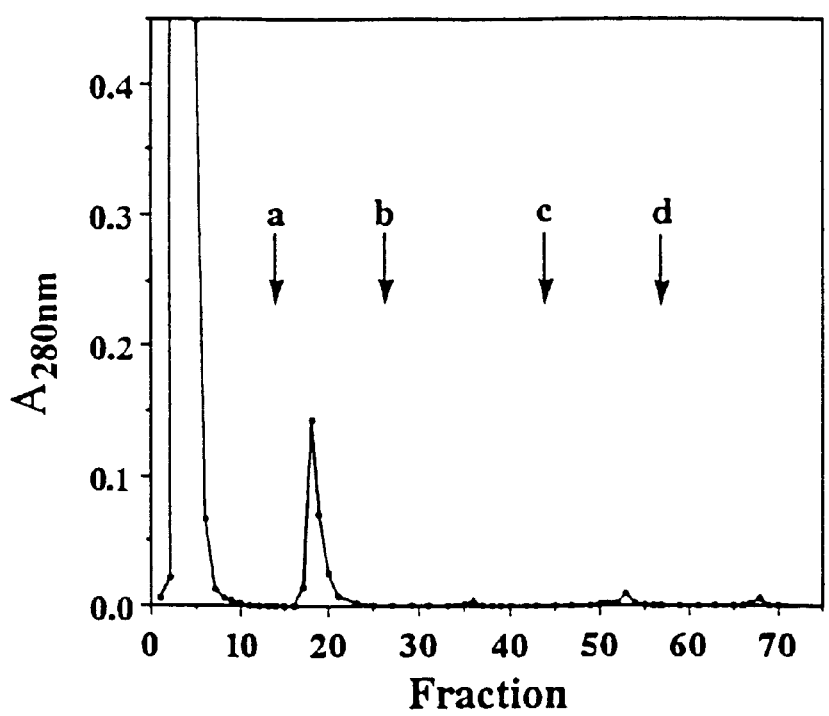

Referring to FIG. 1(B), the dialyzed solution was applied to a Ins(1,4,5)$P_3$-agarose column (5.8 ml bed volume) equilibrated with 10 mM Tris buffer, pH 7.5. The column was washed with equilibrating buffer followed by, in sequence, (a) 15 ml of 500 mM NaCl in the same buffer, (b) 30 ml of 100 mM glycine buffer, pH 3.5, (c) 15 ml of 10 mM Tris buffer, pH 8.8, and (d) 35 ml of 100 mM $NaHCO_3$/$Na_2CO_3$ buffer, pH 10.5. Fractions of 1.7 ml were collected. Fractions 66–69, exhibiting anti-Ins(1,4,5)$P_3$ antibody activity, were pooled, concentrated, and dialyzed against 10 mM Tris buffer, pH 7.5.

These affinity-purified antibodies showed much improved selectivity between Ins(1,4,5)$P_3$ and Ins(1,3,4,5)$P_4$, with $IC_{50}$ values of 12 nM and 730 nM, respectively. The differential affinity, as indicated by the ratios of $IC_{50}$ values, increased from 2- to 60-fold.

Figure 2:
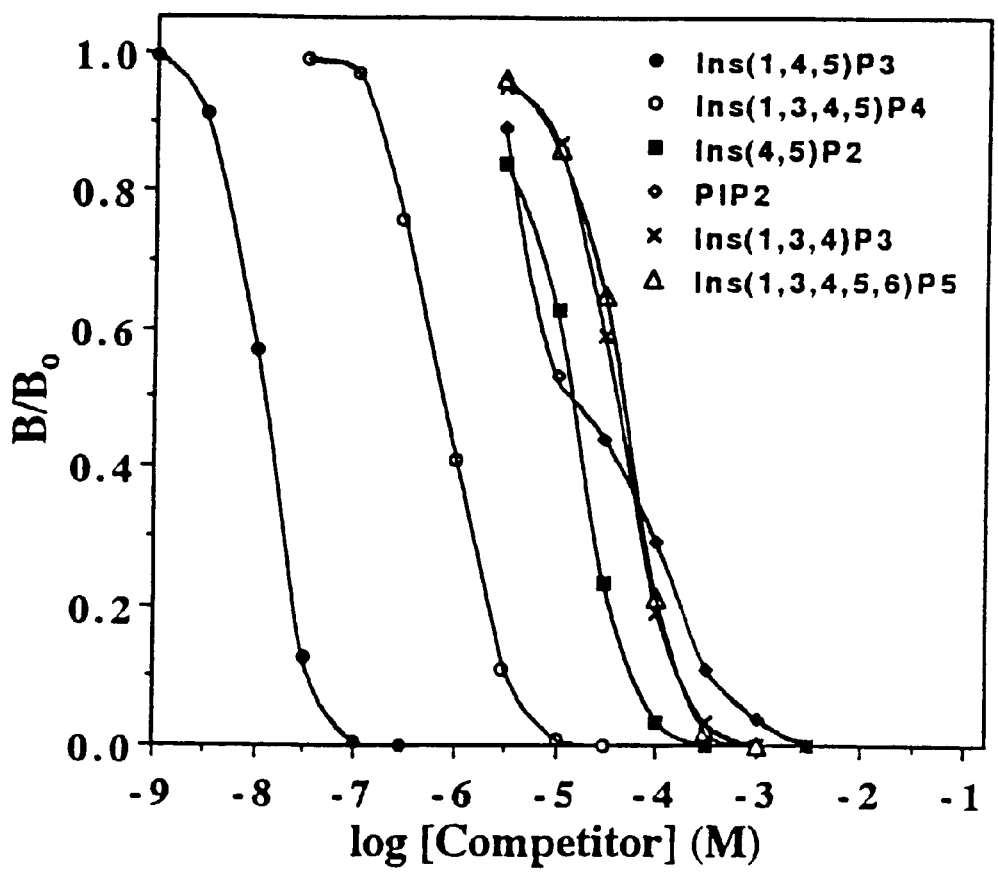
FIG. 2 is a graph of Inositol phosphate specificity of affinity-purified antibodies.

Referring to FIG. 2, the displacement curves were generated from competitive ELISA experiments between immobilized (1,4,5)$IP_3$ and various inositol phosphates shown in the insert. The antibodies were preincubated with individual competitors at various concentrations for 30 minutes at room temperature before added to the (1,4,5)$IP_3$ immobilized EIA plates. The assay for the competitive binding was the same as that described for the ELISA under "Experimental Procedures". Percentage total specific binding is expressed by $B/B_o$, where B=absorbance with competitor and $B_o$=absorbance without competitor. Each data point represents the means of three determinations. For clarity, the standard deviations were not shown.

$IC_{50}$ values for other inositol phosphates are: Ins(4,5)$P_2$, 14 μM; $PIP_2$, 14 μM; Ins(1,3,4)$P_3$, 39 μM; Ins(1,3,4,5,6)$P_5$, 45 μM, which are three orders or magnitude higher than that of Ins(1,4,5)$P_3$.

Nonspecific Inhibition of Ins(1,4,5)$P_3$-antibody Interactions by Multivalent Ions In view of the electrostatic nature of Ins(1,4,5)$P_3$-antibody recognition, the interaction might be interfered by anions that competitively bound to the positively charged active domain of the antibodies in a nonspecific manner. FIG. 5 shows that the binding between the affinity-purified antibodies and the immobilized Ins(1,4,5)P$_3$ was inhibited by a number of polyanionic substances at high concentrations. The IC$_{50}$ values for individual inhibitors were: ATP$^{4-}$, 0.21 mM; HPO$_4^{2-}$, 2.61 mM; SO$_4^{2-}$, 11.6 mM.

Figure 3:
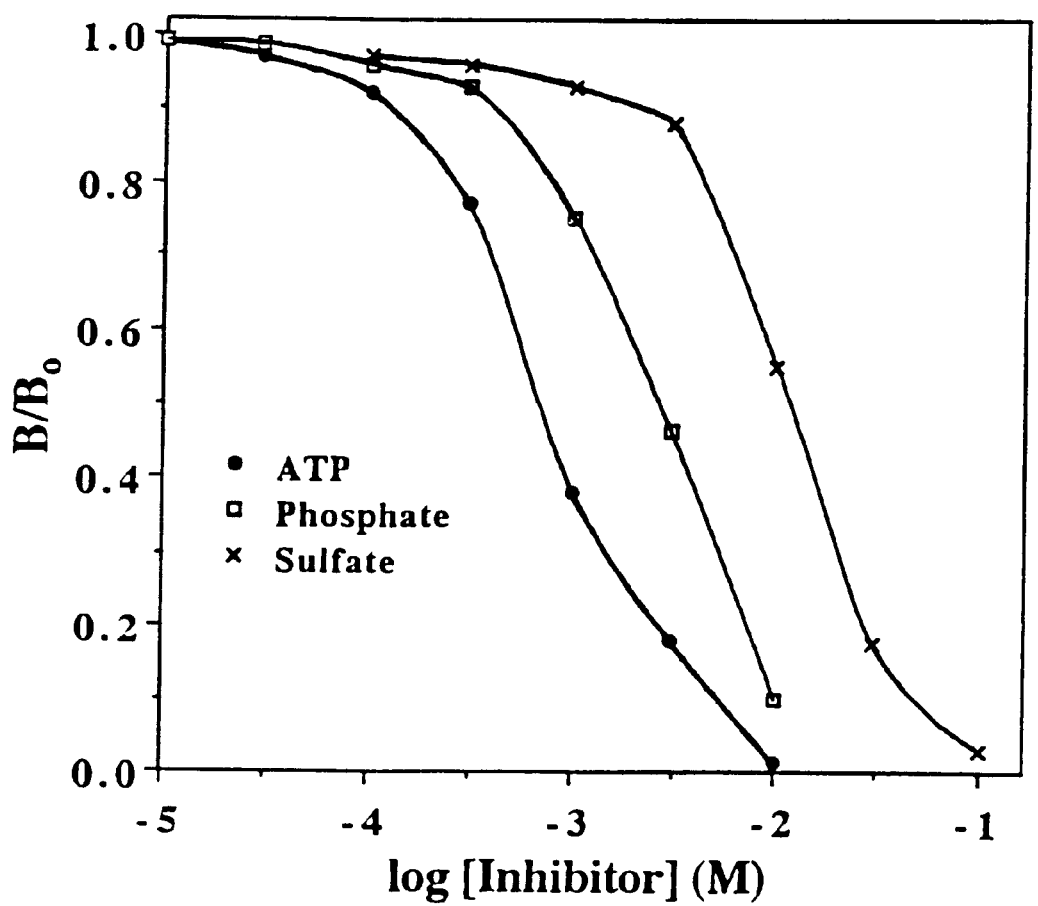
FIG. 3 is a graph of the inhibition of antibody binding to immobilized Ins(1,4,5) P$_3$ by multivalent anions.

Referring to FIG. 3, the affinity-purified antibodies were preincubated with individual multivalent ions at indicated concentrations for 30 minutes at room temperature before added to the (1,4,5)IP$_3$ immobilized EIA plates. The counterion for all the anions tested is Na+ which showed no inhibiting effect on the binding. The assay for the binding inhibition was the same as that described for the ELISA in the Experimental Procedures. Percentage maximal antibody binding is expressed by B/B$_o$, where B=absorbance with inhibitor and B$_o$=absorbance without inhibitor. Each data point represents the means of three determinations.

However, no appreciable interference was noted with haparin up to 0.3 mM, nor were with other monovalent anions such as N$_3$− and Cl−. Cations such as K+, Na+, NH$_4$+, and Tris at concentrations up to 100 mM did not cause significant inhibition to the antibody recognition.

Discussion

The invention is directed to the preparation of anti-Ins(1, 4,5)P$_3$ antibodies through immunizing rabbits with covalent Ins(1,4,5)P$_3$-BSA conjugates. Both IP$_3$-C$_6$NC$_5$-BSA and IP$_3$-C$_5$-BSA were able to generate antibodies with a high degree of specificity for Ins(1,4,5)P$_3$. Both antiserum preparations showed discriminative binding toward Ins(1,4,5)P$_3$, but also cross-reacted with Ins(1,3,4,5)P$_4$ with one-third of the affinity. Other inositol phosphates including Ins(1)P$_1$, Ins(4,5)P$_2$, Ins(1,3,4)P$_3$, Ins(1,5,6)P$_3$, Ins(1,2,5,6)P$_4$, IP$_6$, Ins(3,4,5,6)P$_4$, and PIP$_2$ failed to effect sufficient molecular interactions with the antibodies, and thus exhibited much lower affinity by two to four orders of magnitude.

The problem in cross-reaction with Ins(1,3,4,5)P$_4$ could be overcome by affinity purification of the antisera on Ins(1,4,5)P$_3$-agarose. This affinity matrix is distinctly different from other types of Ins(1,4,5)P$_3$-based affinity absorbents reported in the literature, Prestwich, G. D.; Marecek, J. F.; Mourey, R. J.; Theibert, A. B.; Ferris, C. D.; Dannof, S. K.; and Snyder, S. H. (1991) *J. Am. Chem. Soc.* 113, 1822–1825; and Tegge, W.; and Ballou, C. E. (1992) *Carbohydr. Res.* 230, 63–77. The three phosphate functions of the immobilized Ins(1,4,5)P$_3$ are freely exposed, enabling the optimal interaction with the binding proteins. The degree of discrimination between Ins(1,4,5)P$_3$ and Ins(1,3,4,5)P$_4$ for the affinity-purified antibodies was comparable to that for Ins(1,4,5)P$_3$ receptors. Nahorski and his coworkers recently reported that Ins(1,3,4,5)P$_4$ was about 40-fold weaker than Ins(1,4,5)P$_3$ at displacing specific [$^3$H]Ins(1,4, 5)P$_3$ binding from Ins(1,4,5)P$_3$ receptors, Wilcox, R. A.; Challiss, R. A. J.; Baudin, G.; Vasella, A.; Potter, B. V. L.; and Nohorski, S. R. (1993) *Biochem. J.* 294, 191–194. The reported IC$_{50}$ values for the tetrakis- and tris-phosphates were 762 nM and 20.7 nM, respectively, which are in line with those obtained with the purified antibodies. This cross interaction may be attributed to the largely shared structural motifs between these two polyphosphates.

The molecular basis of ligand recognition for these antibodies is analogous to that of Ins(1,4,5)P$_3$ receptors, arising from the complementary interactions involving ion pairing and hydrogen bonding between the binding domain and the hapten. The binding of the antibodies to immobilized Ins(1, 4,5)P$_3$ could be disrupted by a number of unrelated multivalent anions including ATP$^{4-}$, HPO$_4^{2-}$, SO$_4^{2-}$ at high concentrations, while no significant inhibition was noted with monovalent ions. However, unlike Ins(1,4,5)P$_3$ receptors, the interaction between the antibodies and the ligand was not affected by heparin up to 0.3 mM. These findings suggest that multivalent anions bound to and neutralized the charges of basic amino acid residues inside the IP$_3$ binding domain. This inhibition is noteworthy because use of any of these anions during the antibody preparation and immunoassay will lead to false negative results. In our study, attempts to enrich the antibodies using (NH$_4$)$_2$SO$_4$ precipitation resulted in a complete loss of binding capability even after extensive dialysis. In the literature, inhibition of binding by multivalent anions has also been reported for Ins(1,4,5)P$_3$ receptors. The antagonistic action of heparin in Ins(1,4,5)P$_3$-induced Ca$^{2+}$ mobilization is well understood, Hill, T. D.; Berggren, P.-O.; Boynton, A. L. (1987) *Biochem. Biophys. Res. Commun.* 149, 897–901; Guillemette, G.; Lamontagne, S.; Boulay, B.; and Mouillac, B. (1989) *Mol. Pharmacol* 35, 339–344; Joseph. S. K.; and Rice, h. L. (1989) *Mol. Pharmacol.* 35, 355–359; and Ghosh, T. K., Eis, P. S.; Mullaney, J. M.; Ebert, C. L.; and Gill, D. L. (1988) *J. Biol. Chem.* 362, 11075–11079. Also, nucleotides and phosphate have been reported to inhibit the binding of Ins(1,4,5)P$_3$ to the receptor from the cerebellar membrane, Willcocks, A. L.; Cooke, A. M.; Potter, B. V. L.; and Nohorski, S. K. (1987) *Biochem. Biophys. Res. Commun.* 146, 1071–1078; and Maeda, N.; Kawasaki, T.; Nakade, S.; Nobutaka, Y.; Takahisa, T.; Kasai, M.; and Mikoshiba, K. (1991) *J. Biol. Chem.* 266, 1109–1116. Evidently, the inhibition of Ins(1,4,5)P$_3$ binding by various multivalent anions further underscores the analogy of the antibody binding to the receptor recognition. On the other hand, cations such as K+, Na+, etc. did not affect the binding.

A technical note worth mentioning is the ELISA developed in this study. In our initial experiments, IP$_3$-C$_6$NC$_5$-casein, prepared in the same manner as that described for our BSA conjugate, was coated to regular microtiter plates through adsorption. These plates failed to bind selectively with IP$_3$ antibodies, and did not respond to competitive binding experiments by free IP$_3$ in a concentration-dependent manner. This lack of specific binding may be attributed to (a) the presence of antibodies directed against C$_6$NC$_5$-linker, or (b) the lack of adsorption of IP$_3$-C$_6$NC$_5$-casein to polystyrene surface due to high charge density. Consequently, with the IP$_3$ molecules covalently attached to the microtiter plates as described, these potential interferences were circumvented.

The utility of anti-Ins(1,4,5)P$_3$ antibodies is 3-fold. First, the ELISA developed here offers an easy quantitative analysis of Ins(1,4,5)P$_3$. Second, antibodies directed against phosphatidylinositol and PIP$_2$ have been applied to probing the intracellular transduction mechanism in various types of cells involving PIP$_2$ as a second messenger precursor, Matuoka, K.; Fukami, K.; Nakanishi, O.; Kawai, S.; and Takenawa, T. (1988) *Science* 239, 640–643; Fukami, K.; Matsuoka, K.; Nakanishi, O.; Yamakawa, A.; Kawai, S.; and Takenawa, T. (1988) *Proc. Natl. Acad. Sci. USA* 85, 9057–9061; Huang, C.-L.; Takenawa, T.; and Ives, H. E. (1991) *J. Biol. Chem.* 266, 4045–4048; and Loirand, G.; Faiderbe, S.; Baron, A.; Geffard, M.; and Mironneau, J. (1992) *J. Biol. Chem.* 267, 4312–4316. These anti-Ins(1,4, 5)P$_3$ antibodies developed by us now add a new line of biological probes for examining the actions of Ins(1,4,5)P$_3$ and its metabolites. Third, the recent development of the anti-idiotypic mimicry of biological ligands has become a useful tool in studying receptor functions, Gaulton, G. N.;

and Greene, M. I. (1986) *Ann. Rev. Immunol.* 4, 253–280; and Linthicum, D. S.; and Farid, N. (eds) (1988) in *Anti-idiotypes, Receptors and Molecular Mimicry*, Spring-Verlag, New York; pp. 1–322. Certain anti-idiotypic antibodies have been demonstrated to mimic biological activities of endogenous ligands by acting as internal images. Examples include anti-idiotypic antibodies against glutamate, Duce, I. R.; Budd, T. C.; and Richardson, P. J. (1991) *Biochem. Soc. Trans.* 19, 143–146, dopamine, Mons. N.; Dubourg, P.; Messier, C.; Chiavaroli, C.; Calas, A.; and Geffard, M. (1991) *J. Hirnforsch.* 32, 617–625, substance P, Couraud, J. Y.; Maillet, S.; Grassi, J.; Frobert, Y.; and Pradelles, P. (1989) *Methods Enzymol.* 178, 275–300, and platelet activating factor, Wang, C.-J.; and Tai, H.-H. (1991) *J. Biol. Chem.* 266, 12372–12378.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. An antigenic compound which is an analogue of D-myo-inositol 1,4,5-triphosphate conjugated to BSA having the structure:

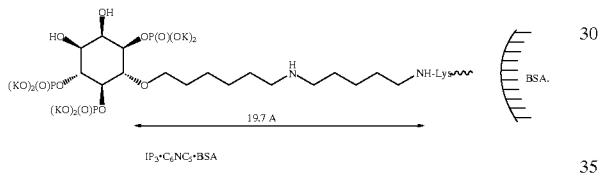

IP$_3$•C$_6$NC$_5$•BSA

2. An antigenic compound which is an analogue of D-myo-inositol 1,4,5-triphosphate conjugated to BSA having the structure of:

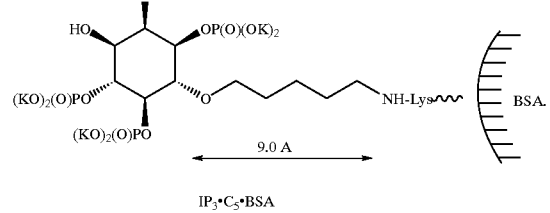

IP$_3$•C$_5$•BSA

3. An ELISA for the detection of anti-Ins(1,4,5)P$_3$ antibodies which comprises:

providing a maleic anhydride-activated polystyrene surface;

attaching the D-myo-inositol 1,4,5-triphosphate analogue of claim 1 or claim 2 to the activated surface via a C-6 linkage to form an affinity matrix;

incubating the sample with the affinity matrix; and detecting antibodies bound to the affinity matrix.

4. An affinity matrix for an ELISA assay which comprises:

a maleic anhydride-activated polystyrene having the D-myo-inositol 1,4,5-triphosphate analogue of claim 1 or claim 2 attached thereto.

* * * * *